United States Patent [19]

Chiang

[11] 3,933,854

[45] Jan. 20, 1976

[54] 3-(INDOL-3-YL)DEHYDRONAPHTHALIDE HYDROCHLORIDES

[75] Inventor: Yunn H. Chiang, Woburn, Mass.

[73] Assignee: Polaroid Corporation, Cambridge, Mass.

[22] Filed: Dec. 3, 1973

[21] Appl. No.: 420,931

[52] U.S. Cl. .................. 260/326.13R; 260/326.12 R; 260/326.14 R; 260/326.15; 96/29 D

[51] Int. Cl.[2] ................ C07D 209/18; C07D 209/20

[58] Field of Search ........... 260/326.13 R, 326.12 R

*Primary Examiner*—Lewis Gotts

*Assistant Examiner*—S. P. Williams

*Attorney, Agent, or Firm*—Sybil A. Campbell

[57] ABSTRACT

This invention is concerned with a novel class of protonated compounds, namely, 3-(indol-3-yl)dehydronaphthalide hydrochlorides, with their synthesis by the reaction of a 3-(indol-3-yl)naphthalide and a high-potential quinone in an inert anhydrous aprotic solvent in the presence of a carboxylic acid catalyst, and with the synthesis of indole naphthalide indicator dyes by reacting the said dehydronaphthalide hydrochlorides and an indole in an aromatic hydrocarbon solvent in the presence of a carboxylic acid catalyst.

4 Claims, No Drawings

3-(INDOL-3-YL)DEHYDRONAPHTHALIDE HYDROCHLORIDES

BACKGROUND OF THE INVENTION

1. Field of the Invention

This invention relates to the preparation of certain indole naphthalein indicator dyes, to intermediates useful in the preparation of such dyes and to a method of synthesizing the intermediates.

2. Description of the Prior Art

Dyes which undergo a change in spectral absorption characteristics in response to a change in pH are well known in the art and frequently are referred to as indicator or pH-sensitive dyes. Typically, these dyes change from one color to another, from colored to colorless or from colorless to colored on the passage from acidity to alkalinity or the reverse and are commonly employed in analytical chemical procedures to measure changes in pH value. Among the indicator dyes most widely used is the group derived from phthaleins.

A particularly useful method of preparing phthalein indicator dyes including indole phthalides and naphthalides and intermediates useful in the preparation thereof form the subject matter of copending U.S. patent applications Ser. Nos. 108,662 and 393,798 of Alan L. Borror filed Jan. 21, 1971 and Sept. 4, 1973, respectively. According to this method, indole phthalides and naphthalides are prepared (1) by reacting (a) an indole and (b) phthalaldehydic or naphthalaldehydic acid to form the corresponding (na)phthalidyl-substituted indole; (2) oxidizing the (na)phthalidyl-substituted indole to the corresponding oxidation product and (3) reacting the oxidation product with an indole, preferably, in the presence of an acid catalyst to yield the corresponding dye product. The expression "(na)phthalidyl" is intended to denote either the corresponding phthalidyl- or naphthalidyl-substituted indole depending upon the selection of phthalaldehydic or naphthalaldehydic acid.

The present invention is concerned with an improvement in the above method which is especially useful and convenient for producing indole naphthaleins on a commercial scale.

SUMMARY OF THE INVENTION

It is, therefore, the primary object of the present invention to provide an improved method of synthesizing 3,3-di-(indol-3-yl)naphthalides.

It is another object to provide novel compounds useful as intermediates in the production of these naphthalides.

It is a further object to provide a method of synthesizing the novel intermediates.

Other objects of this invention will in part be obvious and will in part appear hereinafter.

The invention accordingly comprises the processes involving the several steps and the relation and order of one or more of such steps with respect to each of the others, and the products and compositions possessing the features, properties and the relation of elements which are exemplified in the following detailed disclosure, and the scope of the application of which will be indicated in the claims.

Specifically, in one embodiment of the present invention, a novel class of protonated quinone methides are prepared by reacting a 3-(indol-3-yl)naphthalide with a high-potential quinone at elevated temperature under anhydrous conditions in an inert aprotic solvent, preferably in the presence of an organic carboxylic acid. In another embodiment of the present invention, the protonated quinone methides thus prepared are reacted with an indole at elevated temperature in certain inert organic solvents, preferably in the presence of an organic carboxylic acid to yield the corresponding 3,3-di(indol-3-yl)naphthalide.

For a fuller understanding of the nature and objects of the invention, reference should be had to the following detailed description.

DESCRIPTION OF THE PREFERRED EMBODIMENTS

According to the present invention, it has been found that a 3-(indol-3-yl)dehydronaphthalide hydrochloride is obtained directly as the oxidation product when the oxidation of a 3-(indol-3-yl)naphthalide with a high-potential quinone, for example, o-chloranil is carried out in a hydrocarbon solvent, preferably in the presence of a specified amount of a carboxylic acid, such as glacial acetic acid. The formation of a compound having the structure of a protonated quinone methide under these conditions was indeed surprising and quite unexpected. Indole compounds having a structure of this type are little known in the chemical literature, and it is believed that the reaction mechanism involving the loss of hydrogen chloride from a chlorinated compound which results in the formation of the subject quinone methide hydrochlorides has not beeen reported previously.

Because of the unexpected structure, the exact nature of the oxidation process and the source of the chloride ion was examined as follow: 2,6-lutidine (0.01 mole) in 75 mls. of xylene containing 3.0 gms. of glacial acetic acid was refluxed in the presence of o-chloranil and then the procedure repeated using tetrahclorocatechol instead of o-chloranil. When o-chloranil was used, a large amount of tarry material was obtained but no chloride ion was detected after workup. On the other hand, when tetrachlorocatechol was employed with lutidine, instead of o-chloranil, a positive chloride test (with silver nitrate) was obtained from the water extract of the reaction mixture. In addition, no tetrachlorocatechol was detected in the reaction mixture. On the basis of these observations, it is believed that hydrogen chloride is generated from the dehydrochlorination of tetrachlorocatechol in the course of the oxidation of the 3-(indol-3-yl) naphthalide resulting in the formation of the quinone methide hydrochloride as the oxidation product.

Though not essential, the subject oxidation preferably is conducted in the presence of an organic carboxylic acid which has been found to catalyze the reaction. For example, in the oxidation of 3-(7-carboxyindol-3-yl)naphthalide with o-chloranil using xylene as the solvent, the reaction tended to the sluggish and did not reach completion in the absence of a carboxylic acid even after refluxing for five hours. The quinone methide hydrochloride oxidation product obtained was of inferior quality, being contaminated with unoxidized 3-(7-carboxyindol-3-yl)naphthalide starting material and with o-chloranil and tetrachlorocatechol which could not be completely removed by washing with ether or with ethyl acetate and tetrahydrofuran. Also, the yield of oxidation product was only about 45 to 50%. In comparison, almost quantitative yields (98–99%) of pure quinone methide hydrochloride were realized when the oxidation reaction was repeated in the presence of a carboxylic acid, for example, when about 3 grams of acetic acid was used in 75 mls. of xylene as based on 0.01 mole of 3-(7-carboxyindol-3-yl)naphthalide. As the high potential quinone, o-chloranil, p-chloranil or dichlorodicyanoquinone may be used, but the best results were obtained with o-chloranil in an aromatic hydrocarbon solvent.

Typical quinone methide hydrochlorides that may be produced in the manner discussed above are those represented by the following formula.

(A)

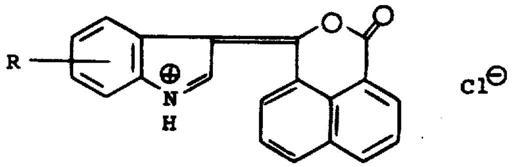

wherein R substituted in the 4-, 5-, 6- or 7-position of the indol-3-yl moiety is hydrogen or a monovalent group, such as, alkyl having 1 to 20 carbon atoms, alkoxy having 1 to 20 carbon atoms, aryl selected from phenyl and naphthyl, alkaryl containing 1 to 20 carbon atoms selected from alkyl-substituted phenyl and alkyl-substituted naphthyl, aralkyl containing 1 to 20 carbon atoms selected from phenyl-substituted alkyl and naphthyl-substituted alkyl, said alkyl, alkoxy, aryl, alkaryl and aralkyl groups being unsubstituted or substituted with, for example, lower alkyl, lower alkoxy, hydroxy, carboxy, sulfo, amino, nitro, halo and cyano. Other R groups include trifluoromethyl, bis-trifluoromethylcarbinol, sulfo, sulfonamido, sulfamoyl, sulfonyl, amido, acyl and its derivatives, amino and its derivatives, nitro, cyano, halo, hydroxy, and carboxy and its derivatives.

Because of their utility in the production of certain naphthalide indicator dyes found particularly useful as photographic optical filter agents, the quinone methide hydrochlorides of the subject invention preferably are substituted in the 7-position with certain groups as represented by the formula:

(B)

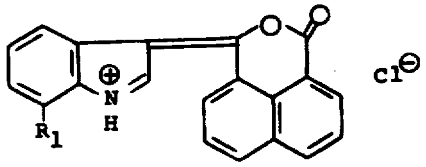

wherein $R_1$ is hydrogen or a group selected from sulfonamido, sulfamoyl, o-hydroxyphenyl, bis-trifluoromethylcarbinol nitro, cyano and particularly carboxy and its derivatives, i.e., COX wherein X is —OR' or —NR' 'R''' and each of said R', R'' and R''' is hydrogen or a hydrocarbon group containing 1 to 20 carbon atoms selected from alkyl, such as, methyl, ethyl, butyl, octyl, hexadecyl and eicosyl; aryl, such as, phenyl and naphthyl; aralkyl, such as, benzyl, phenethyl, phenylhexyl, phenyldodecyl and other phenyl-substituted alkyl groups; and alkaryl, such as, propylphenyl, octylphenyl, decylphenyl, dodecylphenyl and other alkyl-substituted phenyl groups.

The 3-(indol-3-yl)naphthalides useful in the preparation of the corresponding quinone methide hydrochlorides according to the subject oxidation may be represented by the formula:

(C)

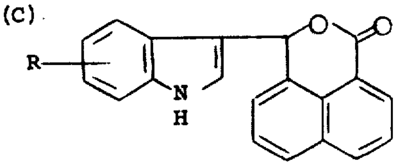

wherein R has the same meaning given in formula A and preferably, R=$R_1$ as defined in formula B.

Illustrative examples of 3-(indol-3-yl)dehydronaphthalide hydrochlorides of the present invention are as follows:

(1)

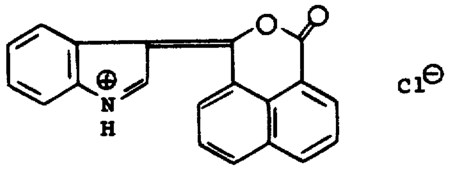

(2)

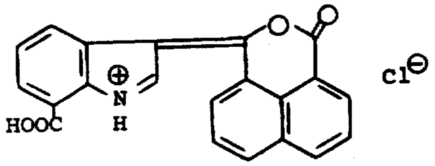

(3)

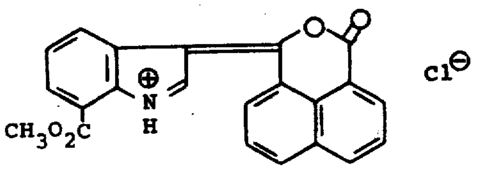

(4)

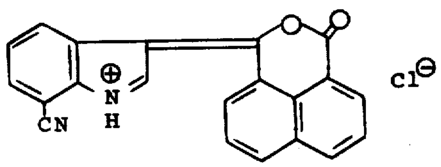

(5)

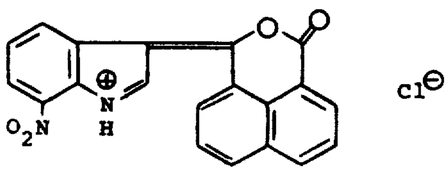

(6)
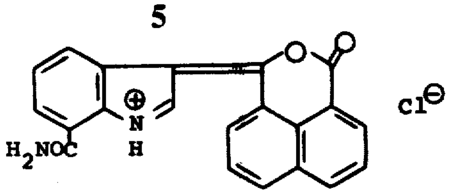
(7)
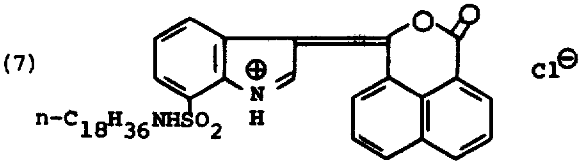
(8)
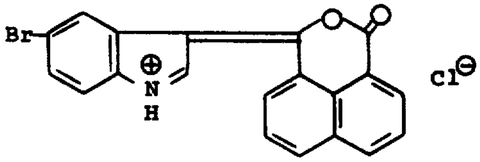
(9)
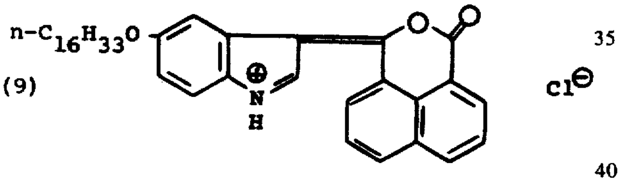
(10)
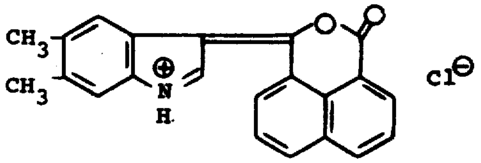
(11)
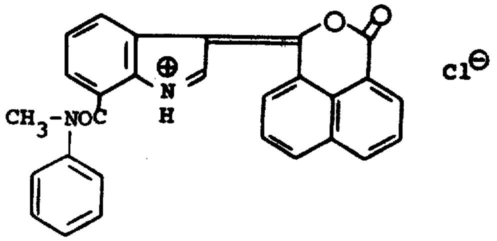
(12)
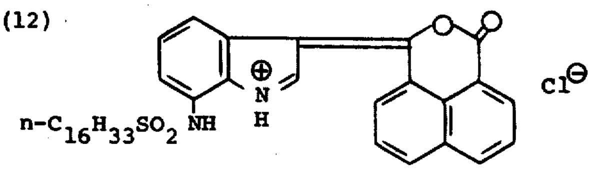
(13)
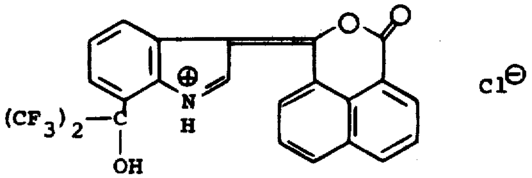
(14)
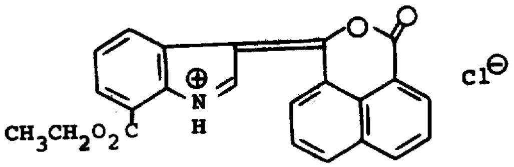
(15)
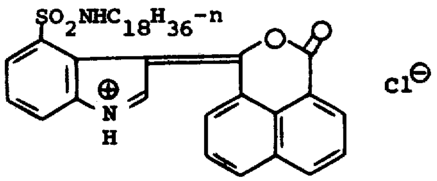
(16)
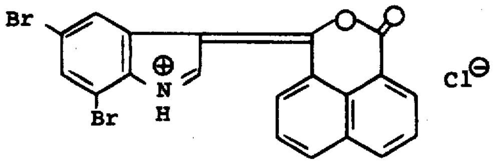

Besides their unexpected formation under the conditions discussed above, the quinone methide hydrochlorides of the present invention, as exemplified by 3-(7-carboxyindol-3-yl) dehydronaphthalide hydrochloride, have shown exceptional reactivity and readily undergo condensation with indoles under various reaction conditions. Indeed, the main advantage of the subject intermediates in that their reaction with indoles in an aromatic hydrocarbon solvent containing a specified amount of carboxylic acid catalyst occurs in substantially quantitative yields. Though the use of an acid catalyst is not essential, it greatly facilitates the reaction to provide more practical reaction times. For example, in the condensation of 3-(7-carboxyindol-3-yl)dehydronaphthalide hydrochloride with a 7-sulfonamidoindole, the reaction was not complete after refluxing for about 16 hours in benzene in the absence of carboxylic acid. However, in the presence of acid, e.g., glacial acetic acid, the reaction was complete in about 2 to 4 hours depending upon the amount of acetic acid present in the reaction mixture.

Any indole may be employed for reaction with the quinone methide hydrochloride intermediates of the present invention provided that the indole is unsubstituted in the 3-position so that it will react with the intermediate to yield the corresponding 3,3-di(indol-3-yl)naphthalide. Suitable indoles and their preparation are found, for example, in *The Chemistry of Heterocyclic Compounds:* Volume 8, Heterocyclic Compounds with Indole and Carbozole Systems, W. C. Sumpter and F. M. Miller, Interscience Publishers, 1954; *The Chemistry of Indoles*, Richard J. Sundberg, Academic Press, 1970.

Typical indoles that may be used in the preparation of the aforementioned indole naphthalides are those represented by the Formula:

(I) 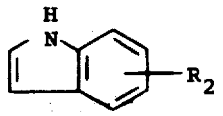

wherein $R_2$ is hydrogen or a monovalent group substituted in the 2-, 4-, 5-, 6- or 7- position, such as, the monovalent groups enumerated above for R. In preferred embodiment, $R_2$ is substituted in the 2- and preferably in the 7-position and is selected from sulfonamido, sulfamoyl, o-hydroxyphenyl, bis-trifluoromethylcarbinol, nitro, cyano and $CO_2X$ wherein X has the same meaning given above.

The method of the present invention for preparing indole naphthalides is illustrated below:

(a)

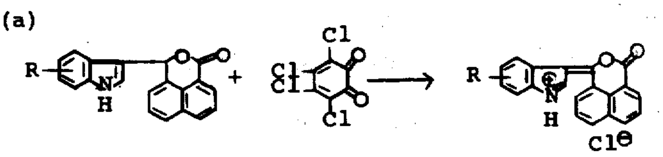

(b)

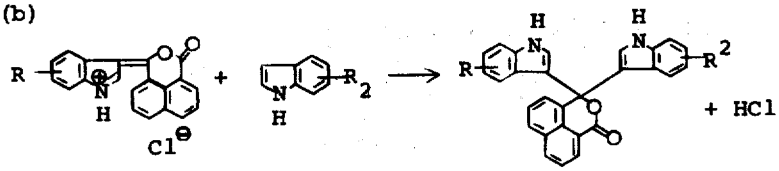

Specific examples of 3,3-di(indol-3-yl)naphthalides that may be prepared according to the present invention are as follows:

(17)

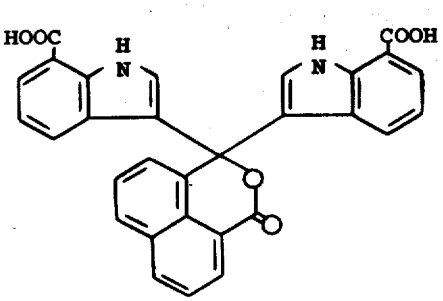

(18)

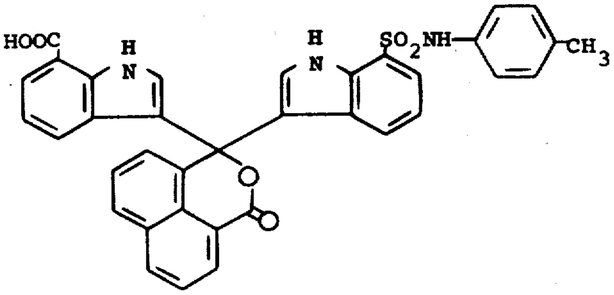

(19)
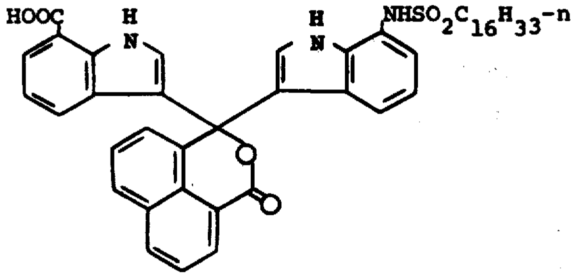
(20)
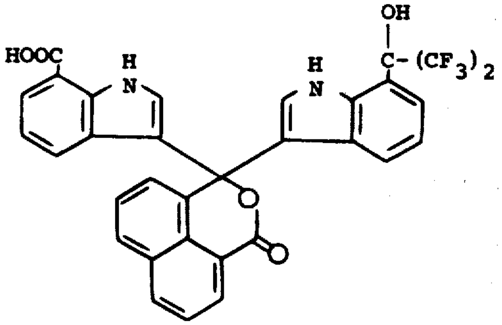
(21)
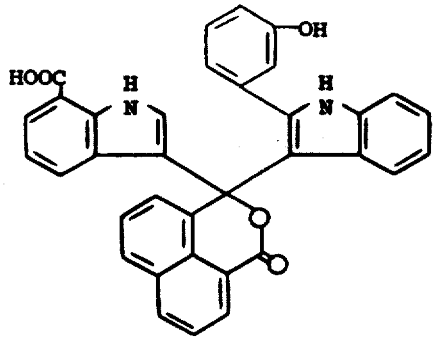
(22)
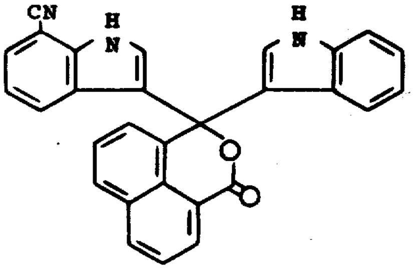
(23)
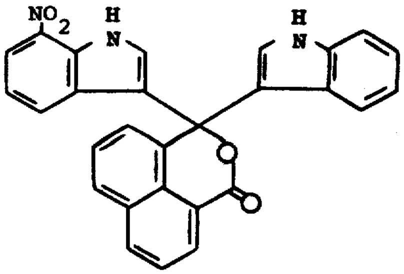

(24)
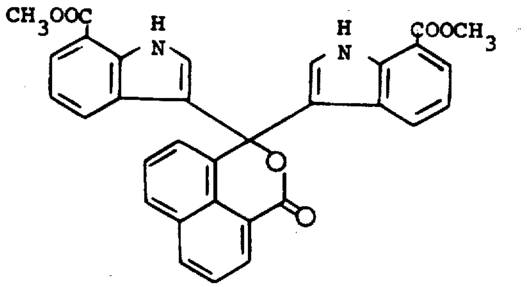
(25)
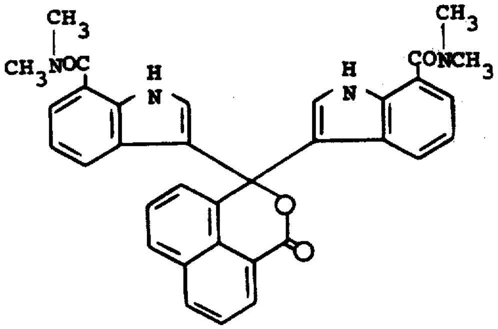
(26)
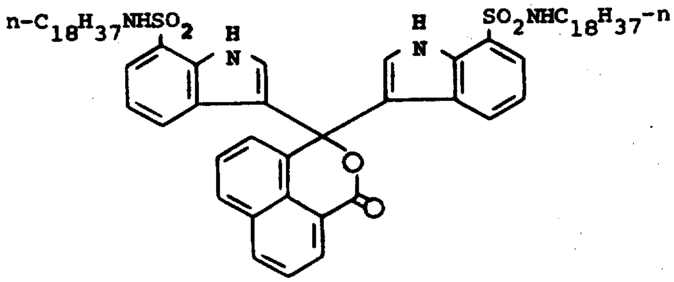
(27)
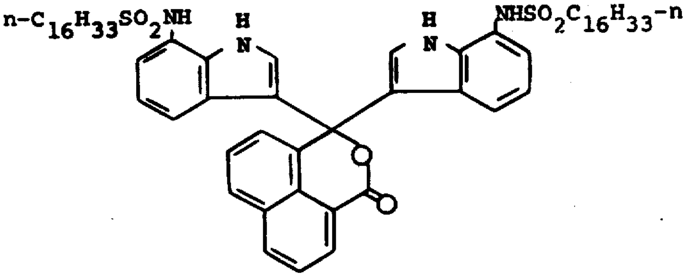
(28)
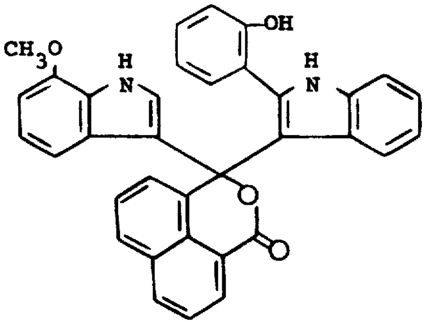

(29)
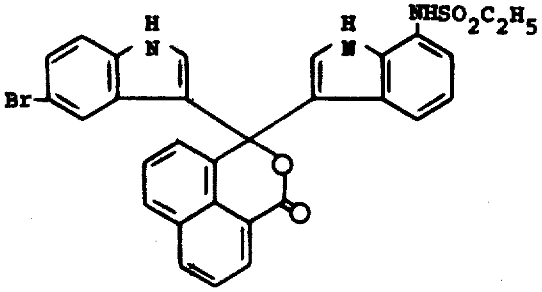
(30)
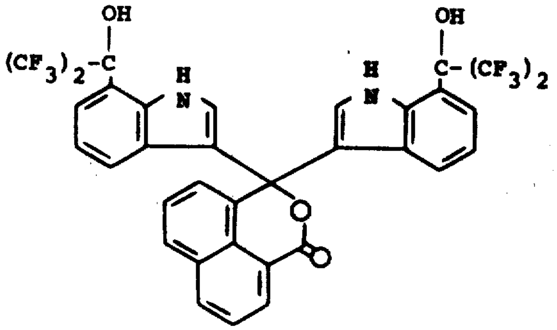
(31)
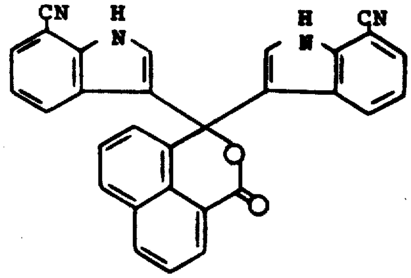
(32)
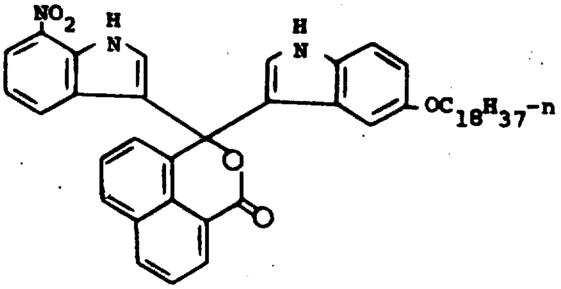
(33)
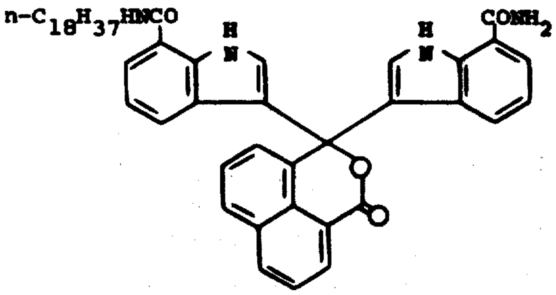

(34)

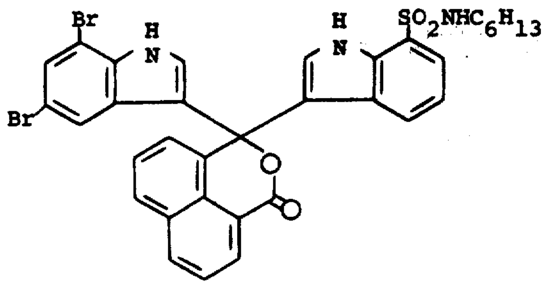

(35)

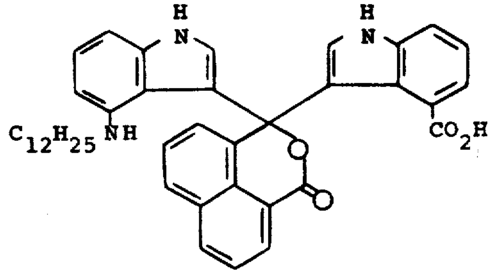

(36)

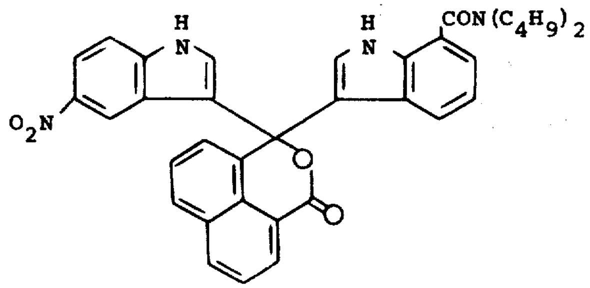

In preparing the quinone methide hydrochlorides of the present invention, the 3-(indol-3-yl)naphthalide selected as the starting material and o-chloranil are reacted in an inert anhydrous aprotic solvent. Though any such solvent may be employed, a hydrocarbon solvent is preferred and particularly an aromatic hydrocarbon solvent, such as, benzene, toluene and xylene. Though the reaction temperature may vary over a relatively wide range, to achieve practical reaction times the oxidation is usually conducted at a temperature between about 100° and 200°C. Particularly satisfactory results have been obtained by refluxing the 3-(indol-3-yl)naphthalide and o-chloranil in xylene (reaction temperature about 145°C.) The use of xylene as the reaction solvent gave the advantages of high purity of the protonated product (by TLC and melting point) of consistent and repeatable high yields and of easy removal of excess o-chloranil oxidizing agent and tetrachlorocatechol by-product by washing the quinone methide hydrochloride with ethyl acetate.

As discussed above, in a preferred embodiment an organic carboxylic acid is used to catalyze the oxidation reaction. For this purpose, any organic carboxylic acid may be employed, for example, aliphatic and aromatic monocarboxylic acids, such as, benzoic acid, toluic acids, halo-substituted benzoic acids, propionic acid and butyric acid. For convenience and economy, however, it is preferred to use glacial acetic acid.

In the oxidation reaction, the amount of solvent employed may vary between about 6 and 10 liters per mole of 3-(indol-3-yl)naphthalide. The amount of carboxylic acid may vary between about 200 and 500 grams per mole of naphthalide, and in all cases, the ratio of acid to solvent should be between about 1:12 and 1:50 grams/ml. In the preferred embodiment employing xylene as the solvent and glacial acetic acid as the catalyst, particularly satisfactory results have been achieved using 250 to 350 grams of acetic acid in 7.5 liters of xylene. The o-chloranil should be used in at least a 40% excess over the naphthalide, and preferably, is used in an amount of between about 1.5 and 2.5 moles per mole of 3-(indol-3-yl)naphthalide. At least a 40% excess of relatively pure o-chloranil (melting range 127°-129°C.) is necessary to ensure completion of the oxidation reaction, and with less pure o-chloranil, a large excess of oxidizing agent should be employed, for example, about 2.0 moles to 2.5 moles of o-chloranil per mole of 3-(indol-3-yl) naphthalide.

In another embodiment of the present invention, the quinone methide hydrochlorides produced in the manner detailed above are condensed with an indole to form the corresponding 3,3-di(indol-3-yl)naphthalide dye products by conducting the condensation reaction in an aromatic hydrocarbon solvent, preferably in the presence of an organic carboxylic acid. The reaction temperature may vary between about 80° and 150°C., and ordinarily, the condensation is carried out by refluxing the quinone methide hydrochloride and indole in an aromatic hydrocarbon, such as, benzene, toluene and xylene selected to give a reaction temperature at reflux within the aforementioned range. Particularly satisfactory results have been achieved using benzene.

Though toluene and xylene at reflux temperature and at lower reaction temperatures of 80°C. and 92°C. gave the dye product in yields between about 85 and 90% by weight (for the condensation step), the dye product contained a high $R_f$ component (by TLC), whereas benzene possessed the unique property of removing this impurity from the dye product while still giving high yields in the vicinity of 90 to 95% by weight.

In the condensation reaction, the solvent is employed in an amount between about 5 and 7.5 liters as based on 1.0 mole of quinone methide hydrochloride. Since the quinone methide hydrochlorides generally are insoluble in aromatic solvents, such as, benzene, it may be desirable to use the larger volumes of solvent in large-scale reactions to improve the dispersion of the quinone methide hydrochloride in the solvent and to reduce the deposition of this material on the walls of the reaction vessel.

As noted above, the condensation preferably is conducted in the presence of a carboxylic acid. Though any of the organic carboxylic acids enumerated above may be used to catalyze the condensation reaction, glacial acetic acid is preferred since it is convenient and economical and has given particularly satisfactory results.

The amount of organic acid may vary between about 300 and 800 grams per mole of quinone methide hydrochloride, and to ensure good quality and high yield of indicator dye product, the ratio of acid to solvent should be greater than 4 gms/75 mls. Preferably, the ratio of acid to solvent ranges between about 5:75 and 6:75 gms/mls.

The indole and quinone methide hydrochloride may be reacted in substantially equimolar proportions, or the indole may be used in a small excess of up to about 0.5 mole as based on 1.0 mole of quinone methide hydrochloride.

In the course of the condensation reaction, hydrogen chloride gas is being liberated. The presence of this strong acid in the medium was found to be beneficial in the first phase, i.e., the first 30 to 90 minutes of the reaction. Actually, if base such as triethylamine were added to the condensation medium initially, reduced yield of the condensation product would be observed. However, it is important for the best performance of the condensation that the hydrogen chloride be mostly eliminated or neutralized after the first period, i.e., after 30 to 90 minutes from the beginning of the reaction. This can be achieved in various ways: by physical entrainment, through application of vacuum, sweeping the mixture with an inert gas (such as nitrogen), or by distillation of the reaction mixture. Another way is to neutralize the hydrogen chloride remaining in the reaction mixture after 30 to 90 minutes by the addition of the appropriate amount of a base, such as triethylamine. When all hydrogen chloride is neutralized, a color change from red to brown is observed.

Though various bases may be used for neutralizing the hydrogen chloride, triethylamine has been found particularly useful since it facilitates the growth of crystal size and thus, facilitates the recovery of dye product. For convenience and precision in handling small amounts of triethylamine, it is preferably added to the reaction mixture as a 2% solution (weight/volume) in benzene. The amount of this triethylamine solution added should be between about 300 and 2,000 mls. as based on 1.0 mole of quinone methide hydrochloride which is equivalent to between about 0.6 and 4.0 moles of triethylamine per mole of quinone methide hydrochloride.

The following examples are given to further illustrate the present invention and are not intended to limit the scope thereof.

EXAMPLE 1

Preparation of 3-(7-carboxyindol-3-yl)-3-(7-hexadecylsulfonamidoindol-3-yl)naphthalide.

(1) A mixture of 6.0 g. (0.0375 moles) of 7-carboxyindole, 7.5 g. (0.0375 moles) of naphthaldehydic acid and 36 ml. of glacial acetic acid was heated on a steam bath (internal temperature 92°C.) while stirred mechanically. To the solution was added 12 ml. of 12% solution of p-toluene-sulfonic acid in acetic acid. An immediate precipitation of product was observed. After additional 10–15 minutes, the reaction mixture was cooled to room temperature, filtered and the solid was washed with 40 ml. of glacial acetic acid. The solid was then stirred in 60 ml. of acetone for 30 minutes, filtered, washed with additional 10 ml. of acetone and dried to give 13.10 g. (87.3% by weight theory) of a white solid, melting range 244–5°C.

The acetone filtrate was concentrated to a 35-40 ml. volume and cooled in the freezer; an additional 0.15 g., melting range 242°–5°C. of 3-(7-carboxyindol-3-yl)naphthalide was collected.

(2) A mixture of 4.03 g. (0.01 mole) of 3-(7-carboxyindol-3-yl)naphthalide (as a solvate with $1CH_3CO_2H$), 4.4 g. (0.0179 moles) of o-chloranil (melting range 127°–129°C.), 3 g. of glacial acetic acid, and 75 mls. of xylene was placed in a 300 ml. flask and heated to reflux with vigorous stirring under nitrogen. After refluxing for five hours, the reaction mixture was cooled to room temperature, filtered, and the red solid was washed with three 10 ml. portions of xylene. The solid was then stirred in 75 mls. of ethyl acetate (the solid is added to a stirring ethyl acetate; the alternative addition would cause caking) for one hour, filtered, washed with additional three 10 ml. portions of ethyl acetate and dried to give 3.70 g. (98.0% by weight theory) of 3-(7-carboxyindol-3-yl)dehydronaphthalide hydrochloride as a red solid, melting range 264.5°–265.5°C.

(3) To a sitrring suspension of 63.0 g. (0.15 moles) of 7-(hexadecylsulfonamido)indole in 940 ml. of benzene and 63.0 g. of glacial acetic acid, 54.0 g. (0.1436 moles) of a finely ground 3-(7-carboxyindol-3-yl)-dehydronaphthalide hydrochloride was added at once under a flow of nitrogen gas (rate, 68 cc/min.). After refluxing for 50 minutes, 50 ml. of a 2% w/v solution of triethylamine in benzene was added all at once causing a color change from deep purple to blackish brown. The reaction mixture was refluxed for an additional five minutes, and 600 ml. of benzene was distilled off from the mixture. The stirring was stopped and the mixture was left at room temperature (~28°C.) overnight (about 16 hrs.) The reaction mixture was then diluted with 400 ml. of toluene, filtered, washed with three 100 ml. portions of toluene and dried to give 95.30 g. (88% by weight) of a colorless solid, melting range 219°–220°C. Ten grams of the crude material recrystallized from 170 ml. of ethanol yielded 9.50 g. (95% by weight), of substantially pure 3-(7-carboxyindol-3-yl)-3-(7-hexadecylsulfonamidoindol-3-yl)naphthalide product, melting range 220°–221°C. The overall yield of the purified product was 84% by weight.

EXAMPLE 2

Example 1 was repeated except that step (2) was carried out as follows:

To a mixture of 64.5 g. (0.16 moles) of 3-(7-carboxyindol-3-yl)naphthalide (as a solvate with $1CH_3COOH$) and of 77.6 g. (0.3154 moles) of o-chloranil (melting range 125°-128°C.) was added a solution of 40 g. of glacial acetic acid in one liter of xylene. The xylene suspension was heated to reflux with vigorous stirring under nitrogen. After refluxing for five hours, the reaction mixture was left at room temperature overnight without stirring (approx. 16 hrs.), filtered, and the red solid was washed with 350 ml. (one portion of 150 ml., then two portions of 100 ml.) of xylene. The solid was then stirred in 600 ml. of ethyl acetate (the solid is added to a stirring ethyl acetate) for one hour, then filtered, and washed with additional five 50 ml. portions of ethyl acetate and dried to give 59.40 g. (99% by weight theory) of 3-(7-carboxyindol-3-yl)dehydronaphthalide hydrochloride as a red solid, melting range 264°- 5°C.

EXAMPLE 3

Example 1 was repeated except that step (3) was carried out using 750 mls. of benzene.

EXAMPLE 4

Example 1 was repeated except that in step (3), the 7-(hexadecylsulfonamido)indole and the dehydronaphthalide hydrochloride were refluxed in 750 ml. of xylene as the solvent.

EXAMPLE 5

Example 4 was repeated except that in step (3) toluene was used as the solvent.

Though ethanol has been found to give a high quality product in good yields, the indicator dye product of step (3) may be purified by recrystallization from various other solvents, for example, from other alcohols, such as, isopropyl alcohol, n-propyl alcohol and butyl alcohol. Also, toluene-acetic acid (75 ml./g.) may be employed for this purpose.

The structure of the product obtained in step (2) of Example 1 above was investigated in detail and on the basis of chemical analysis and the spectral and other data set out below was found to be 3-(7-carboxyindol-3-yl) dehydronaphthalide hydrochloride, the structure of formula I.

a. The compound analysed for a formula:

$C_{21}H_{11}NO_4.1HCl$

Most samples contained some amount of water, equivalent to 0 to 0.4 $H_2O$. The amount of hydrochloric acid, as determined on many samples, could be sometimes as low as 0.67 HCl, but on several samples reached values of 0.97 HCl by silver nitrate titration. The fact that a chloride ion titer of 0.97 dropped to 0.90 after six months of storage of a sample, indicated the sensitivity of the quinone methide hydrochloride towards moisture. The low chloride ion titer could be explained by the following equation:

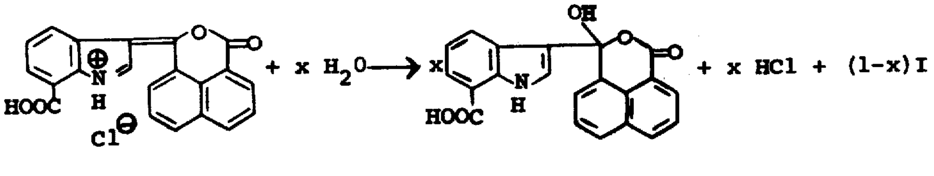

I IV b. Comparisons of the infrared spectrum of I with those of its precursor naphthalide V, of the hydrated form IV and of the known immonium salt VI is tabulated as follows: (in $cm.^{-1}$)

| | —OH | >NH | ≥NH⁺ | >C=O | >C=C—C=N |
|---|---|---|---|---|---|
| I | 3217 | — | 2300 | 1762 | 1668 |
| VI | — | — | 2325 | — | 1627 |
| V | — | 3360 | — | 1690 | — |
| IV | 3218 | 3228 | — | 1698 | — |

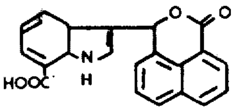

V

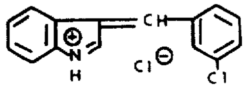

VI

The absorption of I at 2300 cm. and of the immonium salt VI at 2325 $cm.^{-1}$ revealed the amine-salt structure for quinone methide hydrochloride I. The absence of > NH absorption and the presence of 1668 $cm.^{-1}$ band further supported the proposed structure.

c. The visible spectrum of I could be obtained by using trifluoroacetic anhydride as solvent. In alcohols, dimethyl sulfoxide, etc., I (which contains water of hydration) was converted to quinone methide hydrate IV which gives no visible absorption. The maximum absorption of 473 mμ. (ε 841) for I is indicative of the presence of conjugation between the two rings. Compound VI shows $\lambda_{Max.}^{EtOH}$382 mμ.,ε450 in a 50 mm. solution (concentration dependent).

The 7-carboxyindole and 1,8-naphthaldehydic acid used as the starting materials in step (1) are well-known in the art and have been prepared using various procedures. For example, 7-carboxyindole may be synthesized by reductive cyclization of 3-chloro-2-nitrophenylpyruvic acid followed by conversion of the cyclic acid product, 7-chloro-2-indolecarboxylic acid, to 7-cyanoindole and then hydrolyzing the cyano group to yield the desired 7-indolecarboxylic acid as described by H. Singer and W. Shive, J. Am. Chem. Soc., 77, p 5700 (1952). This indolecarboxylic acid also may be synthesized from the corresponding 7-cyanoindoline as described by R. Ikan and E. Rapaport, Tetrahedron, 23, p. 3823 (1967).

The synthesis of 1,8-naphthaldehydic acid by the alkaline cleavage of acenaphthenequinone with aqueous alkaline hydroxide at elevated temperature has been reported by Graebe and Gfeller, Ann. 276, p. 1 (1893), Cason et al., J. Org. Chem. 15, p. 608 (1950) and others. An improved method of preparing 1,8-naphthaldehydic acid at comparatively low temperatures, i.e., at room temperature or thereabouts by using a solvent system of certain aprotic solvents and water forms the subject matter of copending U.S. patent application Ser. No. 336,797 of Henry Bader and Yunn H. Chiang filed Feb. 28, 1973 now U.S. Pat. No. 3,812,115.

Sulfonamidoindoles such as that used in the above

Examples may be prepared in various ways, for example, from indolines as disclosed in copending U.S. patent application Ser. No. 108,663 of Paul S. Huyffer filed Jan. 21, 1971 now U.S. Pat. No. 3,772,329, by reacting a 7-amino-N-acetylindoline with the selected alkyl, aryl, alkaryl or aralkyl sulfonyl chloride to give the corresponding 7-sulfonamido-N-acetylindoline, deacetylating the N-acetylindoline to the corresponding 7-sulfonamidoindoline by acid hydrolysis and converting the 7-sulfonamidoindoline to the corresponding 7-sulfonamidoindole by catalytic dehydrogenation. The 7-sulfonamidoindoles also may by synthesized from 7-nitroindole by reducing the nitro to an amino group and reacting the resulting 7-aminoindole with the selected sulfonyl chloride or anhydride to give the corresponding 7-sulfonamidoindole as disclosed in U.S. Pat. No. 3,297,717.

The advantages afforded by the present invention are numerous. By conducting the oxidation and condensation reactions in the manner detailed above, the quinone methide hydrochlorides and the indole naphthalide dyes are not only obtained in improved yields and purity but also may be isolated from the reaction media with greater ease than was the case previously. Because of the nature of the solvent employed in the oxidation reaction as carried out in the subject process, the previously experienced difficulty of separating the desired oxidized intermediates from the catechol by-products is eliminated. The catechol by-products of the oxidizing agent rather than being mixed in with the protonated quinone methide product are soluble in the reaction medium. Thus, the quinone methide hydrochloride may be isolated using simple filtration techniques, and any catechol or other reaction by-product remaining in association with the filtered solid may be easily removed by recrystallization from an appropriate solvent, for example, ethyl acetate. The indole naphthalide dye also is obtained in substantially improved yields under the conditions employed in the subject condensation reaction, and like the product of the oxidation step, may be recovered with ease. The dye product may be isolated in substantially pure state simply by filtering the reaction mixture. The improvement in yields and purity in both the oxidation and condensation steps together with the ease and convenience in handling the oxidation and condensation products renders the subject invention especially useful for producing indole naphthalide indicator dyes on a commercial scale.

It will be appreciated that the indole naphthalein dyes produced in accordance with the present invention will find utility in titrations and other analytical procedures where phthalein dyes are commonly employed, for example, to measure changes in pH value as reflected by the change in color of the dye from one color to another or from colored to colorless or vice versa. The indicator dyes produced according to the present invention are also useful as optical filter agents in photographic processes for protecting an exposed photosensitive material from post-exposure fogging during development in the presence of incident light. The use of certain dyes derived from indoles including indole naphthalides as photographic optical filter agents forms the subject matter of U.S. Pat. No. 3,702,244, which for convenience, is incorporated herein by reference. The present invention finds particular utility in the production of the indicator dyes disclosed in the aformentioned patent which comprise indole naphthalides wherein at least one and preferably both of the indol-3-yl radicals are substituted with a hydrogen-bonding group, such as, carboxy, o-hydroxphenyl, sulfonamido, sulfamoyl and bis trifluoromethyl carbinol and in the production of indicator dyes substituted with groups readily converted to such a hydrogen-bonding group, such as, nitro, cyano and the groups $CO_2R'$ and CONR''R''' discussed above.

Since certain changes may be made in the above product and processes without departing from the scope of the invention herein involved, it is intended that all matter contained in the above description shall be interpreted as illustrative and not in a limiting sense.

What is claimed is:

1. A compound of the formula:

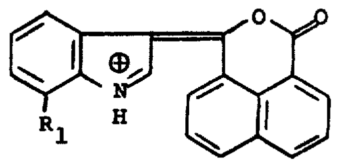

$Cl^{\ominus}$ wherein $R_1$ is hydrogen or a group selected from o-hydroxyphenyl, bis-trifluoromethylcarbinol, nitro, cyano and —COX wherein X is —OR' or —NR''R''' and each of said R', R'' and R''' is hydrogen or a hydrocarbon group slected from alkyl containing 1 to 20 carbon atoms, phenyl, naphthyl, phenyl-substituted alkyl containing up to 20 carbon atoms and alkyl-substituted phenyl containing up to 20 carbon atoms.

2. A compound as defined in claim 1 wherein $R_1$ is —COX.

3. A compound as defined in claim 2 wherein X is OR'.

4. 3-(7-carboxyindol-3-yl)dehydronaphthalide hydrochloride.

* * * * *